United States Patent [19]

Hammett

[11] Patent Number: 5,144,284
[45] Date of Patent: Sep. 1, 1992

[54] PATIENT-MONITORING BED COVERING DEVICE

[76] Inventor: Rawlings H. Hammett, P.O. Box 307, Grandview, Mo. 64030

[21] Appl. No.: 704,113

[22] Filed: May 22, 1991

[51] Int. Cl.$^5$ .......................... G08B 23/00; A61F 5/48
[52] U.S. Cl. .................... 340/573; 128/886; 340/604; 340/666
[58] Field of Search .............. 340/573, 604, 666, 575, 340/521–522; 200/61.05, 85 R; 128/886, 782

[56] References Cited

U.S. PATENT DOCUMENTS

| | | | |
|---|---|---|---|
| 2,818,477 | 12/1957 | Gollhofer | 340/568 X |
| 2,912,977 | 11/1959 | Holbrook | 340/568 X |
| 3,926,177 | 12/1975 | Hardway, Jr. et al. | 340/573 X |
| 3,991,746 | 11/1976 | Hanna | 340/573 X |
| 4,106,001 | 8/1978 | Mahoney | 340/604 |
| 4,129,501 | 12/1978 | Haynes | 340/604 X |
| 4,191,950 | 3/1980 | Levin et al. | 340/604 |
| 4,205,672 | 6/1980 | Dvorak | 128/886 |
| 4,212,295 | 7/1980 | Snyder | 128/886 |
| 4,347,503 | 8/1982 | Vyehara | 340/604 |
| 4,356,818 | 11/1982 | Macias et al. | 128/886 |
| 4,411,034 | 10/1983 | Williams | 340/568 X |
| 4,539,559 | 9/1985 | Kelly et al. | 340/573 |
| 4,614,939 | 9/1986 | Wang | 340/573 |
| 4,706,071 | 11/1987 | Lin | 340/573 X |
| 4,851,816 | 7/1989 | Macias et al. | 340/573 |
| 4,862,144 | 8/1989 | Tao | 340/573 |

Primary Examiner—Jin F. Ng
Assistant Examiner—Thomas J. Mullen, Jr.
Attorney, Agent, or Firm—Norman B. Rainer

[57] ABSTRACT

A bed covering device provides monitoring signals responsive to movement and urination of a person lying upon a bed. The device is constructed of a fitted bedsheet having a perimeter adapted to embrace a mattress, a waterproof sheet disposed above the fitted bedsheet, moisture detectors disposed upon the upper surface of the waterproof sheet, and pressure sensors disposed upon the lower surface of the waterproof sheet. The moisture and pressure sensors generate electrical signals that can be used for monitoring or alerting purposes.

6 Claims, 2 Drawing Sheets

5,144,284

PATIENT-MONITORING BED COVERING DEVICE

BACKGROUND OF THE INVENTION

This invention relates to patient monitoring devices such as used in hospitals and nursing homes and more particularly concerns a bed covering device adapted to detect movement and bedwetting by a patient resting thereupon.

It is common practice in hospitals and other health care facilities for nurses to check the condition of patients at regular intervals ranging typically between one and two hours. The nurse usually peers into the patient's room to observe whether or not the patient is sleeping, and whether any discomfort or serious medical problem exists. Due to increasingly large workloads of floor nurses, it is difficult for them to devote individualized attention to each patient. Between nurse visits, there may be periods where restlessness, discomfort, or physical distress of the patient go unnoticed.

The quality of sleep is often an important consideration in healthcare. A patient may tend to toss-and-turn more during the night due to physical discomfort, resulting in slower recovery or weakened condition. It is therefore desirable to more accurately monitor the movement of the patient upon the bed surface. A system for detecting and recording such movement would enable a nurse to more closely observe a patient's condition, administer medication and sedatives, and report such conditions to attending physicians.

In extreme cases, seriously ill patients can expire during the night and the attending nurse is not aware until the next "rounds" are made. Quite often immediate medical attention at the instant of trauma can save the patient's life. However, it is quite expensive and impractical to maintain a patient in an Intensive Care Unit on constant cardiac, respiratory, and other biological monitoring equipment. Many institutions are not equipped for such care on a routine basis. It is therefore desirable to provide a means for detecting the expiration of a patient and immediately alerting the nurse or doctor to the condition at the moment of trauma.

One biological function which is often triggered upon expiration of a patient is loss of bladder control, resulting in bedwetting. A device for immediately detecting the presence of moisture could discern such trauma immediately and provide an appropriate alarm. Further benefits of alerting an attending nurse that the patient has wet the bed are to prevent discomfort to the patient and promote sanitary conditions.

Various devices have earlier been disclosed for detecting the presence of urine. Numerous devices have been designed to be worn adjacent the body within undergarments or layered therewithin. Generally the detection device is comprised of a multiplicity of electrically conductive surfaces separated by an absorbent non-conductive material. Upon urination, the absorbent material soaks up the electrically conductive urine, thereby completing an electrical circuit which in turn activates an alarm device. However, such moisture monitors are not easily adaptable to use in bed coverings where a substantially flat configuration is required.

It is therefore an object of the present invention to provide a bed covering device having moisture detection means.

It is a further object of the present invention to provide a device of the aforesaid nature which will further monitor movement of a person upon the surface of a bed.

It is another object of this invention to provide a bed covering device of the aforesaid nature of simple, durable construction amenable to low cost manufacture.

These objects and other objects and advantages of the invention will be apparent from the following description.

SUMMARY OF THE INVENTION

The above and other beneficial objects and advantages are accomplished in accordance with the present invention by a bed covering device adapted to cover a mattress and detect urination and movement of a person lying thereupon, said device being adapted for use with a monitoring device capable of detecting closed- and open- circuit conditions and suitably recording signals and alarming an attendant, said bed covering device comprised of:

a) a fitted bedsheet having a perimeter adapted to embrace the edges of said mattress, b) a waterproof compliant detection sheet having upper and lower surfaces and a border which is attached to said fitted bedsheet adjacent the perimeter thereof, said detection sheet adapted to be interposed between said fitted sheet and said person, c) compliant flat moisture detection means removably associated with the upper surface of said detection sheet, said detection means having electrical characteristics that change upon contact with an aqueous fluid, d) compliant flat pressure sensitive means disposed upon the lower surface of said detection sheet for detecting compressive force exerted by said person, and e) electrical connector means emergent from said moisture detection means and said pressure sensitive means and configured to connect in modular fashion with said monitoring device and alarm.

In a preferred embodiment, the detection sheet may have a multiplicity of grommeted apertures about its border adapted to enable the covering device to be tied to the bed.

The moisture detection means may be constructed of paired foil strips separated by a moisture absorbent material such as blotter paper.

Strips of hook and loop type attachment material may be used to fasten the moisture detection means to the detection sheet, thereby allowing quick replacement and laundering of the covering device.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
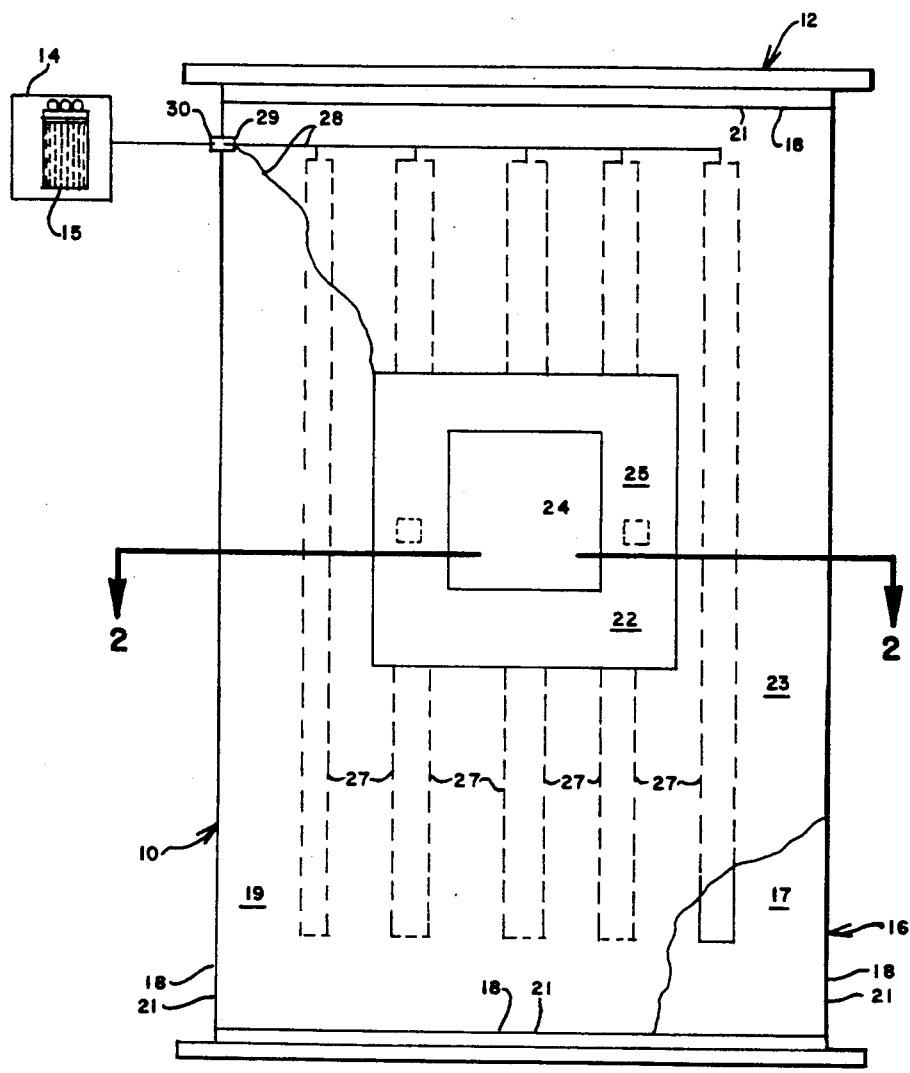
FIG. 1 is a top plan view of an embodiment of the bed covering device of the present invention with portions broken away and shown in operative association with a hospital bed.
Figure 2:
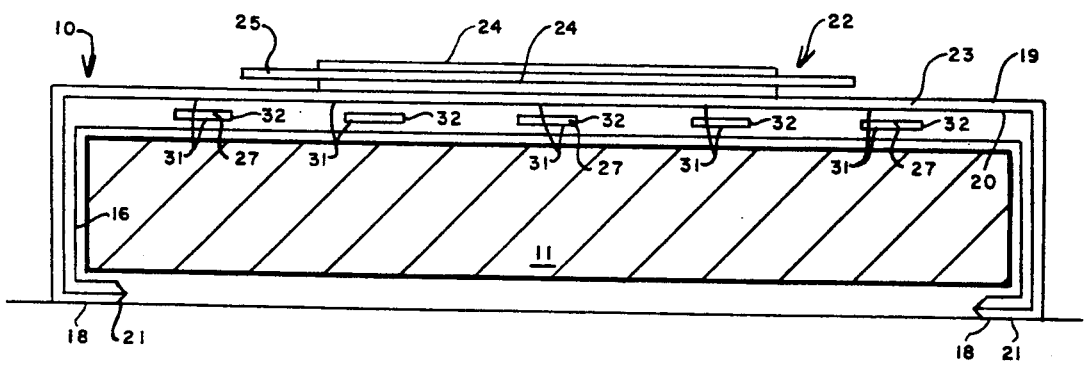
FIG. 2 is an enlarged sectional view taken upon the line 2—2 of FIG. 1.
Figure 3:
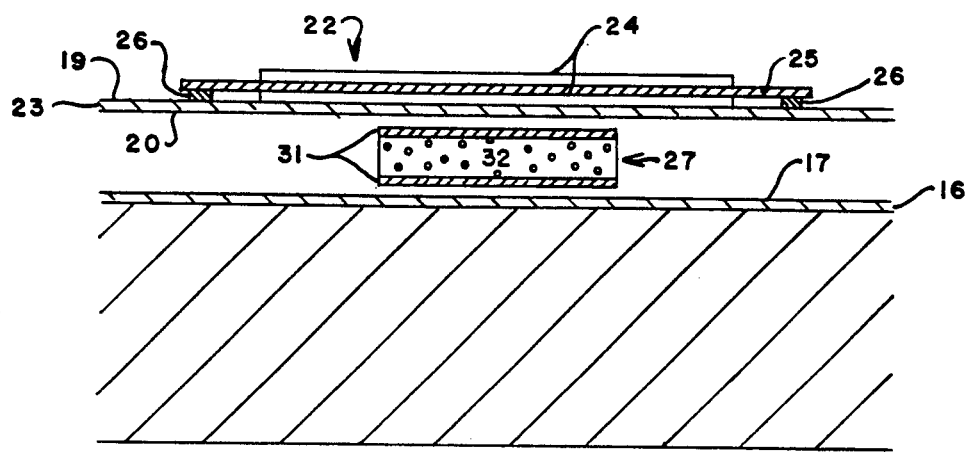
FIG. 3 is an enlarged fragmentary view of the device as shown in FIG. 2.
Figure 4:
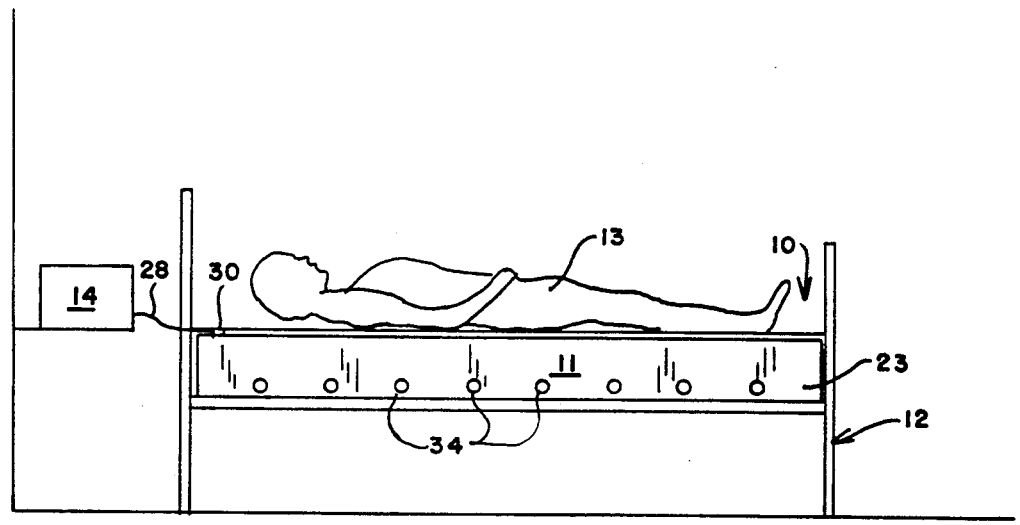
FIG. 4 is a side view of the embodiment of FIG. 1 shown in association with a patient supine upon the bed.

Referring to FIGS. 1-4, an embodiment of the bed covering device 10 of the present invention is shown emplaced upon mattress 11 of hospital bed 12. The device is adapted to detect moisture and the movement of patient 13, and supplies electronic signals to monitoring device 14 capable of detecting closed- and open-circuit conditions. Monitoring device 14 suitably records electronic signals upon a recording device in the form of strip chart recorder 15, and has alarm means (not shown) which may be in the form of a bell, buzzer, or light activated by signals supplied from the bed covering device. Alternatively, the monitoring device may relay appropriate signals to a location remote from the bed.

Bed covering device 10 is comprised of fitted bedsheet 16 having upper surface 17 and perimeter 18 adapted to embrace the edges of mattress 11. A waterproof compliant detection sheet 23, disposed above bedsheet 16, has upper and lower surfaces 19 and 20, respectively, and border 21 bonded to perimeter 18 of bedsheet 16. In a preferred embodiment, the detection sheet may have a multiplicity of grommeted apertures 34 about its border adapted to enable the covering device to be tied to the bed.

Compliant moisture detection means 22 is removably associated with upper surface 19 of detection sheet 23 by means of strips of attachment material 26. Suitable hook and loop type attachment material is commercially available under the trademark VELCRO from the Velcro Corporation of N.Y. Such hook and loop attachment or fastening material are paired interactive members, each comprising a compliant base sheet having an upraised pile of synthetic fibers. The fibers of one member are in the form of loops. The fibers of the other interactive member are cut loops, which constitute hooks. When the two members of the fastening system are pressed together in face-to-face relationship, there is substantial engagement of hook fibers with loop fibers. A considerable effort may be applied to separate the members unless they are peeled apart, in which event the members are easily separated.

In the illustrated embodiment, detection means 22 is comprised of electrically conductive perforated foil strips 24 separated by absorbent blotter paper 25. A low voltage electromotive force such as 3 volts D.C. is applied by way of monitoring device 14 to one extremity of the foil strips. Paper 25 becomes electrically conductive upon moistening by urine from the patient. Current passes through the moistened paper between foil strips 24, thereby providing an electrical signal to monitoring means 14. Detection means 22 may be discarded after use to promote sanitary conditions. In alternative embodiments, detection means 22 may be constructed from cloth, polyurethane foam, or other absorbent materials, in which case the detection means may be retained and laundered between uses. The absorbent material, particularly in the disposable embodiment, may be pretreated with dried salts to enhance conductivity upon moistening. Further alternative embodiments may utilize fine wires woven into cloth material rather than foil strips.

Compliant compressive force sensors 27 are bonded to lower surface 20 of detection sheet 23. In the illustrated embodiment, the sensors are constructed of elongated paired strips of foil 31 separated by a thin layer of polyurethane foam 32 and adapted to closely approach each other under compressive force generated by patient 13 lying thereupon. A low voltage electromotive force is applied to one extremity of foil strips 31. Changes in the electrical resistivity or capacitance between the paired foils are detected by monitoring device 14. In alternative embodiments, sensors 27 may be in the form of thin walled flexible tubing sealed at one extremity and having modular quick-disconnect fittings connected at the other extremity to tubes leading into monitoring device 14. In such embodiments, monitoring unit 14 is equipped with a corresponding multiplicity of bourdon tube type sensing units which are responsive to changes of pneumatic pressure within each tube. Compressive force exerted upon the tube forces the bourdon tube to a less tightly wound position where it activates an appropriate electrical circuit to produce an alerting signal. Moisture detection means 22 and said sensors 27 are connected by wires 28, through modular plug and socket 29 and 30, respectively, to monitoring device 14.

The bed covering device of this invention is also usefully employed in infant's cribs to monitor for possible Sudden Infant Death Syndrome. The device, by virtue of sensors 27, will also detect the unauthorized removal of the infant from the crib.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A bed covering device adapted to cover a mattress and detect urination and movement of a person lying thereupon, said device being adapted for use with a monitoring device capable of detecting closed- and open- circuit conditions and suitably recording signals and alarming an attendant, said bed covering device comprising:
   a) a fitted bedsheet having a perimeter adapted to embrace the edges of said mattress,
   b) a waterproof compliant detection sheet having upper and lower surfaces and a border attached to said fitted bedsheet adjacent the perimeter thereof, said detection sheet adapted to be interposed between said fitted sheet and said person,
   c) compliant flat moisture detection means removably associated with the upper surface of said detection sheet, said detection means having electrical characteristics that change upon contact with an aqueous fluid,
   d) compliant flat pressure sensitive means disposed upon the lower surface of said detection sheet for detecting compressive force exerted by said person, and
   e) electrical connector means emergent from said moisture detection means and said pressure sensitive means and configured to connect in modular fashion with said monitoring device and alarm.

2. The bed covering device of claim 1 wherein said detection sheet has a multiplicity of grommeted apertures about its border to facilitate the anchoring of said device to said bed.

3. The bed covering device of claim 1 wherein said moisture detection means is comprised of paired metal foil strips separated by a moisture absorbent material of uniform thickness.

4. The bed covering device of claim 3 wherein said moisture absorbent material is blotter paper.

5. The bed covering device of claim 3 wherein said pressure sensitive means comprises elongated pairs of strips of metal foil separated by a thin uniform layer of a compressive material.

6. The bed covering device of claim 1 employing strips of hook and loop attachment material to removably fasten said moisture detection means to said detection sheet.

* * * * *